US 6,632,198 B2
(12) United States Patent  (10) Patent No.: US 6,632,198 B2
Caizza  (45) Date of Patent: *Oct. 14, 2003

(54) RETRACTING NEEDLE SYRINGE

(75) Inventor: Richard Caizza, Barry Lakes, NJ (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 27 days.

This patent is subject to a terminal disclaimer.

(21) Appl. No.: 09/932,007

(22) Filed: Aug. 17, 2001

(65) Prior Publication Data

US 2001/0053886 A1 Dec. 20, 2001

Related U.S. Application Data

(63) Continuation of application No. 09/419,184, filed on Oct. 15, 1999, now Pat. No. 6,368,303.

(51) Int. Cl.$^7$ .............................................. A61M 5/24
(52) U.S. Cl. .................... 604/110; 604/198; 604/218; 604/240
(58) Field of Search ................................ 604/110, 181, 604/187, 192, 195, 198, 203, 205, 206, 218, 223, 225, 226, 228, 229, 235, 239, 240, 241–243, 245, 263, 164.01, 197; 222/386

(56) References Cited

U.S. PATENT DOCUMENTS

| 4,233,975 A | 11/1980 | Yerman | 128/218 |
|---|---|---|---|
| 4,687,467 A | 8/1987 | Cygielski | 604/110 |
| 4,838,863 A | 6/1989 | Allard et al. | 604/110 |
| 4,838,869 A | 6/1989 | Allard | 604/195 |
| 4,900,307 A | 2/1990 | Kulli | 604/110 |
| 4,927,414 A | 5/1990 | Kulli | 604/110 |
| 4,929,237 A | 5/1990 | Medway | 604/198 |
| 4,946,446 A | 8/1990 | Vadher | 604/198 |
| 4,955,870 A | 9/1990 | Ridderheim et al. | 604/195 |
| 4,966,593 A | 10/1990 | Lennox | 604/198 |
| 4,973,316 A | 11/1990 | Dysarz | 604/195 |
| 4,994,034 A | 2/1991 | Botich et al. | 604/110 |
| 5,011,476 A | 4/1991 | Foster | 604/110 |
| 5,013,301 A | 5/1991 | Marotta, Jr. et al. | 604/197 |
| 5,019,044 A | 5/1991 | Tsao | 604/110 |
| 5,045,063 A | 9/1991 | Spielberg | 604/110 |
| 5,046,508 A | 9/1991 | Weissler | 128/763 |
| 5,047,017 A | 9/1991 | Koska | 604/110 |
| 5,049,133 A | 9/1991 | Villen Pascual | 604/110 |
| 5,053,010 A | 10/1991 | McGary et al. | 604/110 |
| 5,064,419 A | 11/1991 | Gaarde | 604/195 |
| 5,084,018 A | 1/1992 | Tsao | 604/110 |

(List continued on next page.)

FOREIGN PATENT DOCUMENTS

| GB | 2197792 A | 6/1998 |
|---|---|---|
| WO | WO 00/27450 | 5/2000 |

Primary Examiner—Brian L. Casler
Assistant Examiner—Cris L. Rodriguez
(74) Attorney, Agent, or Firm—Jeanne P. Lukasavag; John L. Voellmicke

(57) ABSTRACT

A retracting needle assembly for use with a syringe barrel having a cylindrical collar and a plunger having a release element with a sharp distal end includes an outer hub having a passageway therethrough and an inner hub having a proximal end, a distal end and a conduit therethrough. The proximal end of the inner hub has an inner portion and a dissociable outer portion connected to the inner portion. The dissociable outer portion is further connected to the outer hub. The distal end of the inner hub is smaller than the passageway of the outer hub at the distal end of the outer hub and projects distally outwardly therefrom. A needle cannula having a distal end, a proximal end, and a lumen therethrough is connected to the inner hub so that the lumen is in fluid communication with the conduit. An energized spring is contained between the inner and outer hub. Structure is provided for connecting the outer hub to the collar of the syringe barrel.

25 Claims, 17 Drawing Sheets

U.S. PATENT DOCUMENTS

| | | | |
|---|---|---|---|
| 5,084,029 A | 1/1992 | Nacci nee Tagliaferri et al. | 604/195 |
| 5,085,640 A | 2/1992 | Gibbs | 604/110 |
| 5,092,853 A | 3/1992 | Couvertier, II | 604/195 |
| 5,114,410 A | 5/1992 | Caralt Batlle | 604/195 |
| 5,180,369 A | 1/1993 | Dysarz | 604/110 |
| 5,180,370 A | 1/1993 | Gillespie | 604/110 |
| 5,188,597 A | 2/1993 | Sweeney et al. | 604/110 |
| 5,188,599 A | 2/1993 | Botich et al. | 604/110 |
| 5,201,710 A | 4/1993 | Caselli | 604/110 |
| 5,211,629 A | 5/1993 | Pressly et al. | 604/110 |
| 5,232,447 A | 8/1993 | Schwarz et al. | 604/110 |
| 5,232,456 A | 8/1993 | Gonzalez | 604/192 |
| 5,267,961 A | 12/1993 | Shaw | 604/110 |
| 5,267,976 A | 12/1993 | Guerineau et al. | 604/198 |
| 5,342,308 A | 8/1994 | Boschetti | 604/110 |
| 5,376,080 A | 12/1994 | Petrussa | 604/198 |
| 5,385,551 A | 1/1995 | Shaw | 604/110 |
| 5,389,076 A | 2/1995 | Shaw | 604/110 |
| 5,395,337 A | 3/1995 | Clemens et al. | 604/110 |
| 5,407,431 A | 4/1995 | Botich et al. | 604/110 |
| 5,407,436 A | 4/1995 | Toft et al. | 604/195 |
| 5,423,758 A | 6/1995 | Shaw | 604/110 |
| 5,487,732 A | 1/1996 | Jeffrey | 604/110 |
| 5,531,694 A | 7/1996 | Clemens et al. | 604/110 |
| 5,533,970 A | 7/1996 | Berger et al. | 604/110 |
| 5,542,927 A | 8/1996 | Thorne et al. | 604/110 |
| 5,562,629 A | 10/1996 | Haughton et al. | 604/158 |
| 5,573,510 A | 11/1996 | Isaacson | 604/158 |
| 5,575,777 A | 11/1996 | Cover et al. | 604/198 |
| 5,578,011 A | 11/1996 | Shaw | 604/110 |
| 5,605,544 A | 2/1997 | Tsao | 604/110 |
| 5,613,952 A * | 3/1997 | Pressly et al. | 604/110 |
| 5,632,733 A | 5/1997 | Shaw | 604/195 |
| 5,634,909 A | 6/1997 | Schmitz | 604/196 |
| 5,637,092 A | 6/1997 | Shaw | 604/110 |
| 5,643,211 A | 7/1997 | Sadowski et al. | 604/110 |
| 5,665,075 A | 9/1997 | Gyure et al. | 604/263 |
| 5,681,292 A | 10/1997 | Tober et al. | 604/195 |
| 5,685,863 A | 11/1997 | Botich et al. | 604/198 |
| 5,769,822 A * | 6/1998 | McGary et al. | 604/110 |
| 5,782,804 A | 7/1998 | McMahon | 604/110 |
| 5,788,677 A | 8/1998 | Botich et al. | 604/195 |
| 5,792,107 A | 8/1998 | Petrocelli | 604/110 |
| 5,800,395 A | 9/1998 | Botich et al. | 604/110 |
| 5,800,403 A | 9/1998 | Pressly, Sr. et al. | 604/195 |
| 5,843,034 A | 12/1998 | Redfern et al. | 604/110 |
| 5,853,390 A | 12/1998 | Freschi | 604/110 |
| 5,882,342 A | 3/1999 | Cooper et al. | 604/195 |
| 5,885,257 A | 3/1999 | Badger | 604/195 |
| 5,902,277 A | 5/1999 | Jentzen | 604/218 |
| 5,908,408 A | 6/1999 | McGary et al. | 604/110 |
| 5,910,131 A | 6/1999 | McGary et al. | 604/110 |
| 5,919,166 A | 7/1999 | McGary et al. | 604/110 |
| 5,921,959 A | 7/1999 | McGary et al. | 604/110 |
| 5,921,960 A | 7/1999 | McGary et al. | 604/110 |
| 5,921,961 A | 7/1999 | McGary et al. | 604/110 |
| 5,935,104 A | 8/1999 | Janek et al. | 604/110 |
| 5,961,491 A | 10/1999 | McGary et al. | 604/110 |
| 5,984,898 A | 11/1999 | Garvin | 604/195 |
| 6,004,278 A | 12/1999 | Botich et al. | 600/576 |
| 6,010,486 A | 1/2000 | Carter et al. | 604/195 |
| 6,036,674 A | 3/2000 | Caizza et al. | 604/195 |
| 6,090,077 A | 7/2000 | Shaw | 604/195 |
| 6,096,005 A | 8/2000 | Botich et al. | 604/110 |
| 6,099,500 A | 8/2000 | Dysarz | 604/110 |
| 6,183,440 B1 | 2/2001 | Bell | 604/110 |

* cited by examiner

RETRACTING NEEDLE SYRINGE

This is a continuation of U.S. application Ser. No. 09/419,184 filed Oct. 15, 1999, now U.S. Pat. No. 6,368,303.

FIELD OF THE INVENTION

The present invention relates to syringes and needle assemblies. More particularly, the present invention relates to a syringe and needle assembly having structure allowing for the automatic withdrawal of the needle cannula into the syringe barrel after use and a method for making the needle assembly.

BACKGROUND

In recent years there has developed an increased concern regarding the transfer of disease, infection or the like to syringe users and healthcare professionals who accidentally or through negligent handling, stick themselves with hypodermic needles while disposing of used hypodermic needle containing products. In many areas in a hospital, where needle cannula products are used, disposal bins are provided so that a syringe or other needle cannula product may be immediately discarded in a safe rigid container. However, there are areas of medical practice, such as emergency rooms, where disposal containers may not be readily available or practical, and where products having self-contained safety features are desirable. In theory, after such a syringe is used to inject medication or for another purpose, a safety device contained within the syringe or needle assembly is activated to prevent further contact with the sharp needle tip. One type of safety syringe includes structure which allows the withdrawal of the hypodermic needle into the syringe barrel to minimize the chance of further contact with the sharp needle tip.

One such prior art retractable needle syringe includes a frangible zone which allows the separation of the forward wall of the barrel, which is connected to the hypodermic needle, from the sidewall of the barrel. The syringe also contains structure on the interior of the forward wall and the exterior of the piston for selectively attaching the piston to the forward wall so that the user can forcibly twist the piston to break the frangible structure and draw the forward wall, including the hypodermic needle, into the syringe barrel. This design requires a compromise in the design of the syringe barrel. The barrel must be strong enough to remain intact during normal use yet weak enough to be sheared apart by any user regardless of strength.

The prior art also includes other retractable needle syringes. These syringes have structure that engages a needle carrier allowing the needle carrier to be forcibly disengaged from the syringe barrel, by action of the plunger rod, and withdrawn into the syringe barrel. Many prior art retractable needle syringes have deficiencies similar to that described above. In particular, the needle or the needle carrier of the retractable needle syringe must be securely held by the syringe barrel during normal use which often includes substantial hydraulic pressures experienced during injection, especially with highly viscous liquids, and forces including piercing rubber stoppers of medication vials. The syringe barrel must hold the needle carrier to a degree that it will not be overcome by the forces of normal use and will still be disengageable through forces applied to a plunger rod which extends from the open proximal end of the syringe barrel. Many prior art retractable needle syringe designs when made with sufficient strength to withstand the forces of normal use have a needle carrier which cannot be easily disengaged. On the other hand, easy disengagement of the needle or the needle carrier can lead to a structure which may not withstand the forces of normal use. This is especially true with needle carriers which are structured to allow a needle assembly to be installed and removed so that the user can select the hypodermic needle size at the time of use. These syringes must also resist the high torque and forces of needle installation and removal. In addition, retractable needle syringes require a two-handed withdrawal procedure which increases the difficulty of use.

The prior art also includes retracting needle syringes which include a spring loaded needle assembly which is held in position during normal use of the syringe assembly and a hollow plunger rod which is sealed during normal use of the syringe assembly so that medication may not enter the plunger rod cavity. These syringes must have structure to allow release of the spring-loaded needle and the opening of the plunger rod cavity so that the needle may enter the plunger rod cavity after the syringe is used for its intended purpose. The retracting needle syringes have similar design problems as those recited hereinabove for retractable needle syringes. In particular, the cavity in the plunger rod must be sealed so that medication cannot enter the plunger rod during use. This seal must sometimes withstand high hydraulic pressures when injecting relatively viscous medication through small needles and still be capable of being easily unsealed and to allow access by the needle assembly. Likewise, the needle assembly must be firmly held in place through the forces of injection and still be disengageable so that it may retract into the syringe barrel and into the plunger rod. Some of the prior art retracting needle syringes use plugs to cover the plunger rod cavity leading to an arguably difficult situation since the plug may fail during the injection process. Likewise, some use plugs to hold the needle assembly in place which can arguably become dislodged during use causing fear of the syringe. In addition, these designs do not allow for a replaceable needle assembly thus depriving the healthcare worker of the option of choosing the appropriate needle size for the injection or procedure being performed. Further, the demand for safety produces such as retracting needle syringes comes with the demand for products that cost little more than a standard syringe assembly. Prior art retracting needle assemblies have shortcomings in that they present designs that cannot be made for a cost that would allow their widespread use because many designs require very precise tolerances as to achieve reliability, and many require assembly processes which can damage the delicate tip of the needle cannula, leading to a high rejection rate.

Although the prior art teaches many different retractable needle syringes and retracting needle syringes having the capacity to withdraw or allow the needle to enter the syringe barrel or the plunger rod, there is still a need for a simple, straight-forward, reliable, easily fabricated retracting needle syringe having adequate structural integrity to withstand the forces of injection, while the spring can still be easily and intentionally released to allow the needle assembly to enter the plunger rod cavity. There is also a need for a retracting needle syringe having replaceable spring-loaded needle assemblies to allow selecting the proper needle size at the time of use and to facilitate prefilling. Also, there is a need for a retracting needle assembly that can be easily assembled in high volume without damaging the delicate cutting tip of the needle cannula.

SUMMARY OF THE INVENTION

An operable retracting needle assembly for use with a syringe barrel having an inside surface defining a chamber, an open proximal end, an open distal end including a cylindrical collar, and a plunger having a release element with a sharp distal edge includes: an outer hub having a proximal end, a distal end and a passageway therethrough, and an inner hub having a proximal end, a distal end and a conduit therethrough. The proximal end of the inner hub includes an inner portion and a dissociable outer portion connected to the inner portion. The dissociable outer portion of the inner hub is connected to the outer hub. The distal end of the inner hub is smaller than the passageway in the outer hub at its distal end and projects distally outwardly therefrom. A needle cannula having a distal end, a proximal end connected to the distal end of the inner hub, and a lumen therethrough. The connection is made so that the lumen is in fluid communication with the conduit of the inner hub. An energized spring is contained between the outer hub and the inner hub. Means for connecting the outer hub to the collar of the barrel such as through threaded engagement, adhesive, ultrasonic welding and the like is provided. The inner and outer hubs are configured so that distal motion of a plunger, having a release element with the sharp distal edge, in a barrel will cause the sharp distal edge of the release element to cut through the portion of the inner hub which separates the dissociable outer portion from the inner portion allowing the spring to move the needle cannula in a proximal direction.

An operable retracting needle assembly may also include a syringe barrel having an inside surface defining a chamber, an open proximal end and an open distal end including a cylindrical collar. The collar includes an outside surface and an inside surface. The outer hub is connected to the collar so that the cannula projects distally outwardly from the syringe barrel. A plunger is slidably positioned in fluid-tight engagement with the inside surface of the barrel. The plunger includes a proximal portion having a distal end with an elongated cavity therein, a release element having a sharp distal edge positioned on the distal end of the proximal portion, and a hollow distal portion releasably connected to the proximal portion and capable of telescopic motion with respect to the proximal portion. A cover element on the distal end of the distal portion seals the distal end of the distal portion. The proximal and distal portions of the plunger are connected so that when distal motion of the plunger with respect to the barrel causes the distal portion to contact structure in the distal end of the barrel additional force will cause the proximal portion of the plunger to separate from the distal portion of the plunger allowing the proximal portion to move distally so that the release element contacts and cuts through the cover element and the inner hub disconnecting the dissociable outer portion from the inner portion and allowing the spring to move the needle cannula far enough into the cavity of the proximal portion of the plunger rod so that the distal end of the cannula is positioned proximally of the distal end of the outer hub.

Another aspect of the present invention is a method of making an operable retracting needle assembly comprising the steps of: providing an outer hub having a proximal end, a distal end and a passageway therethrough; providing an inner hub having a proximal end, a distal end and a conduit therethrough; providing a needle cannula having a distal end, a proximal end, and a lumen therethrough; providing a coil compression spring; assembling the inner hub, the spring and the outer hub so that the spring is compressed and held within the outer hub by the inner hub being connected to the outer hub so that the distal end of the inner hub is accessible from the passageway at the distal end of the outer hub; positioning the proximal end of the cannula in the distal end of the conduit of the inner hub; and applying adhesive in the space between the conduit and the needle cannula.

DETAILED DESCRIPTION

Figure 1:
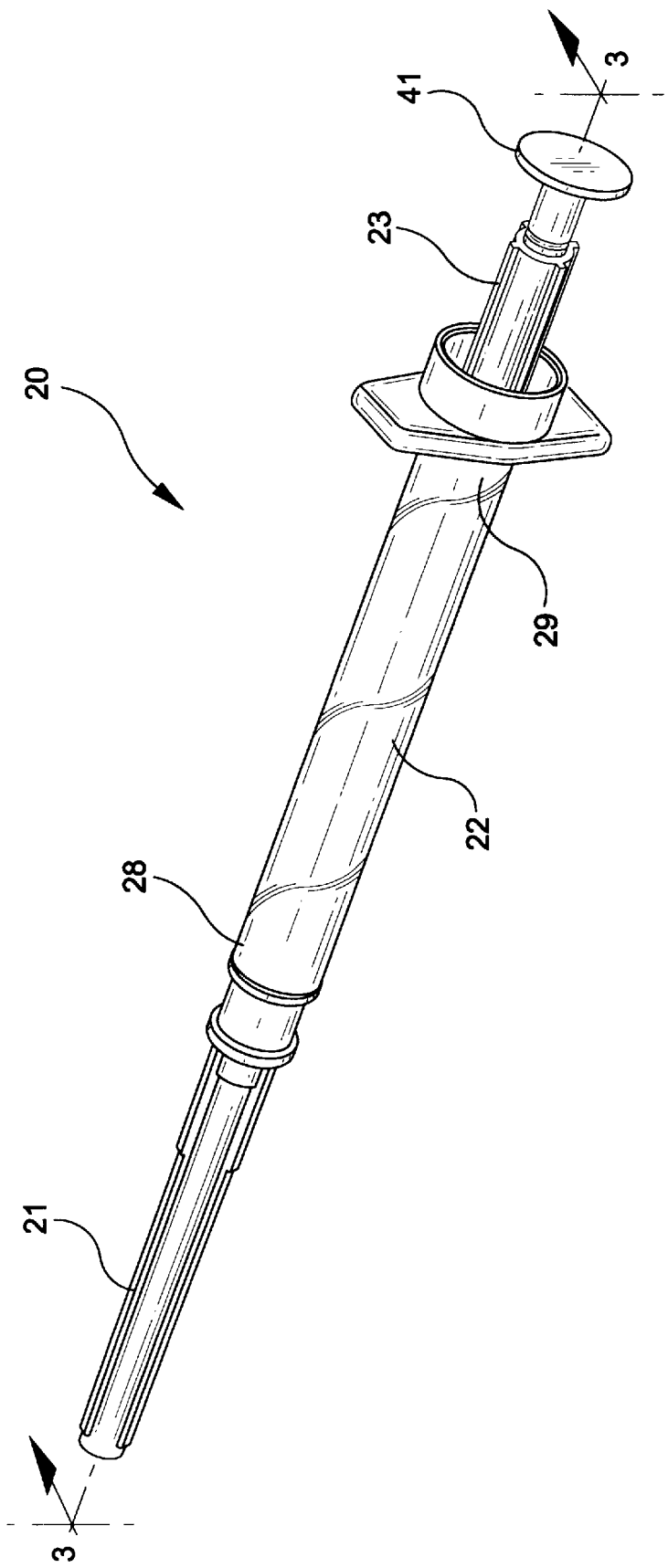
FIG. 1 is a perspective view of the retracting needle assembly and retracting needle syringe of the present invention.
Figure 2:
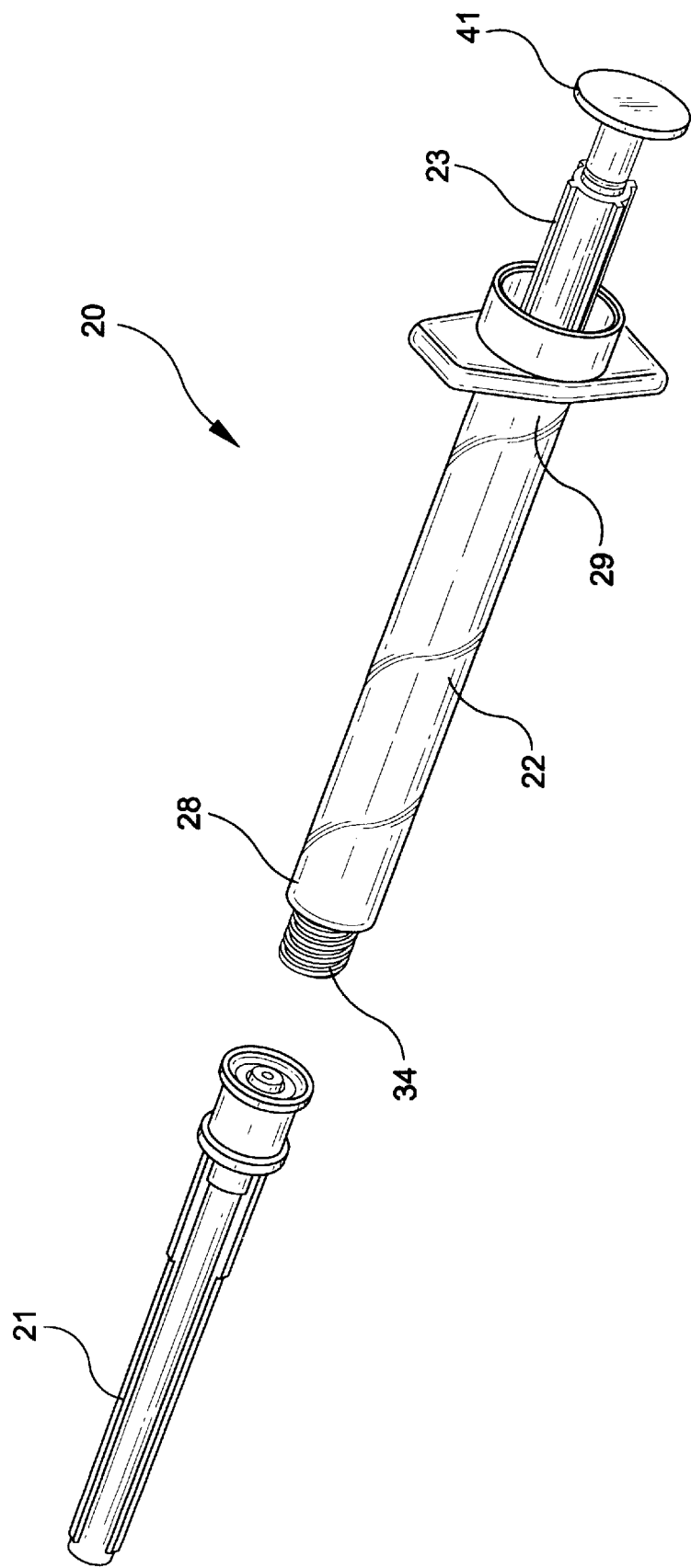
FIG. 2 is the syringe of FIG. 1 illustrating a replaceable needle assembly.
Figure 3:
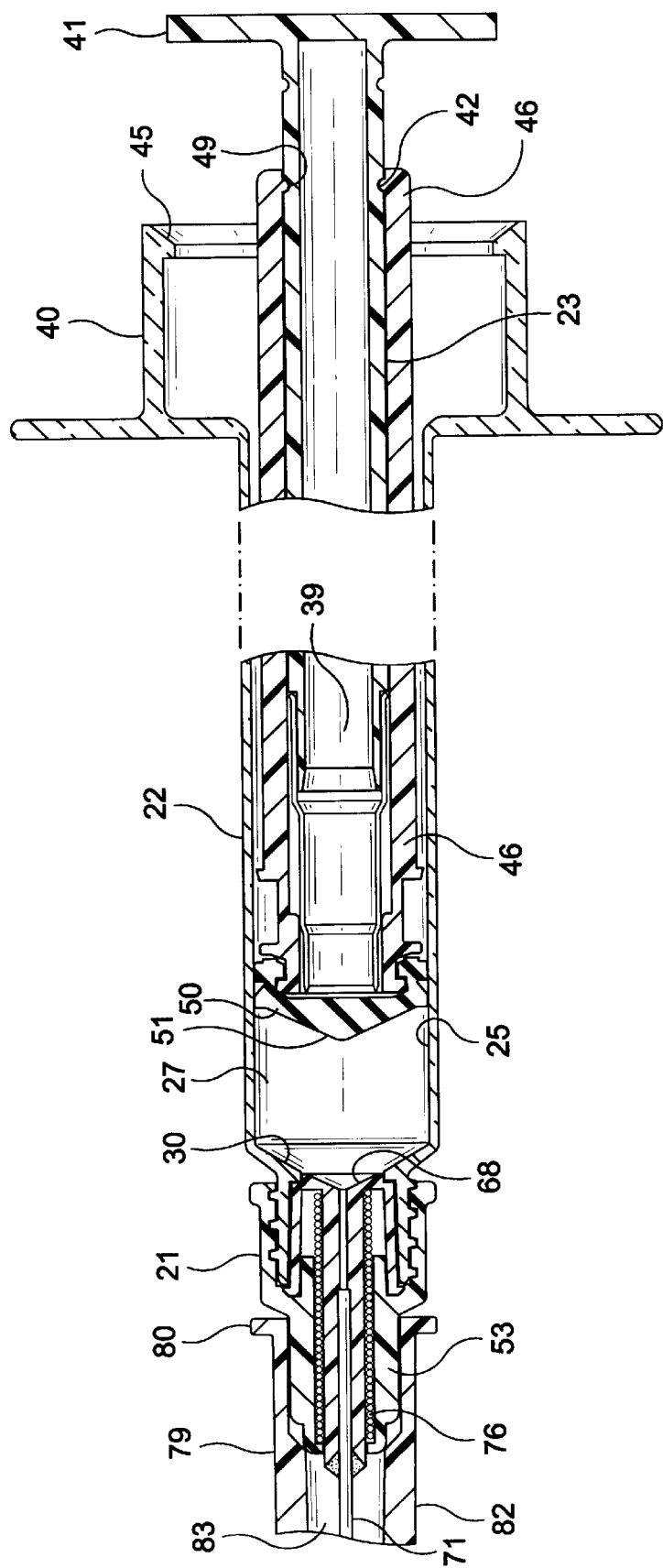
FIG. 3 is a cross-sectional view of the syringe and needle assembly of FIG. 1 taken along line 3—3.
Figure 4:
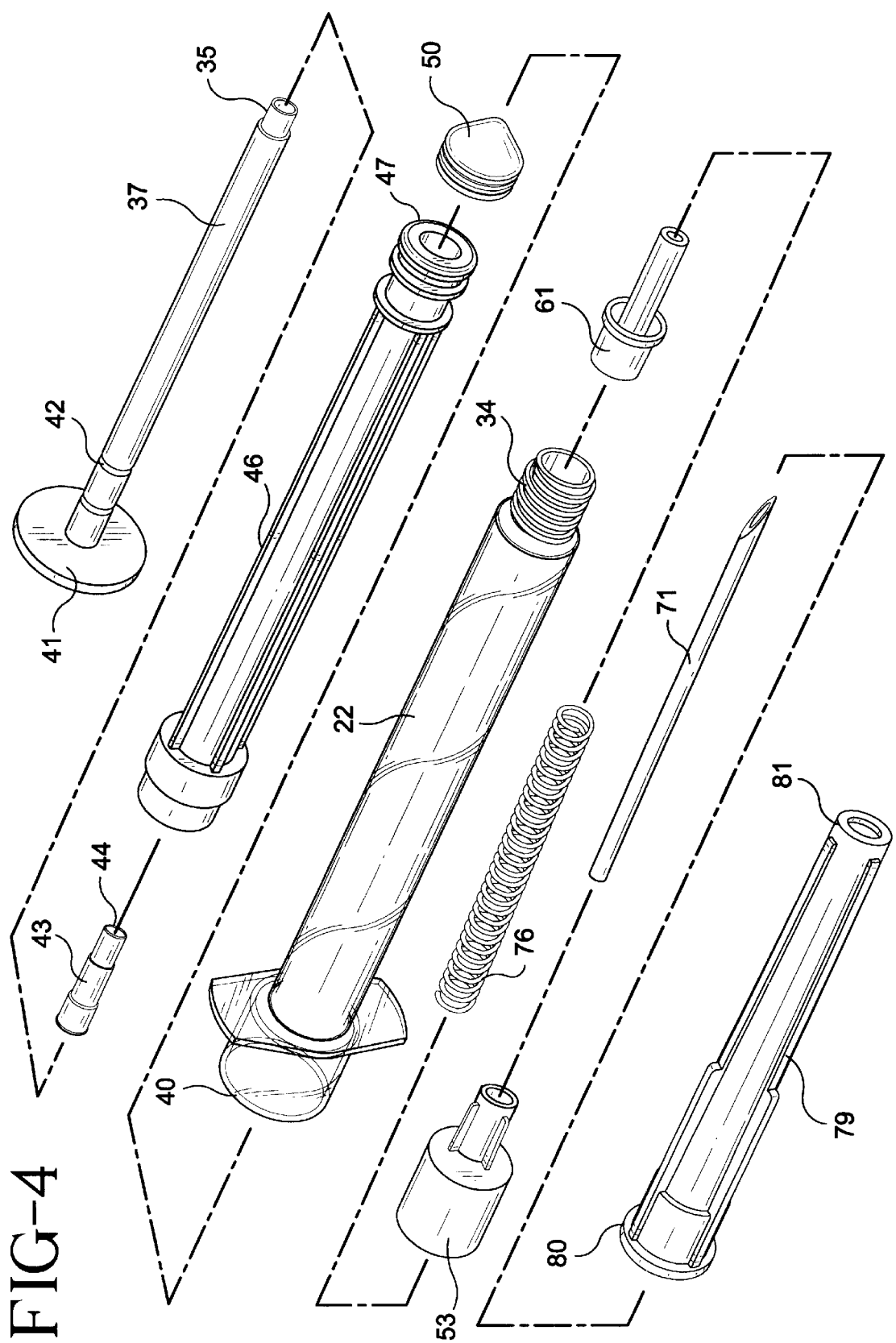
FIG. 4 is an exploded perspective view of the syringe and needle assembly of FIG. 1.
Figure 5:
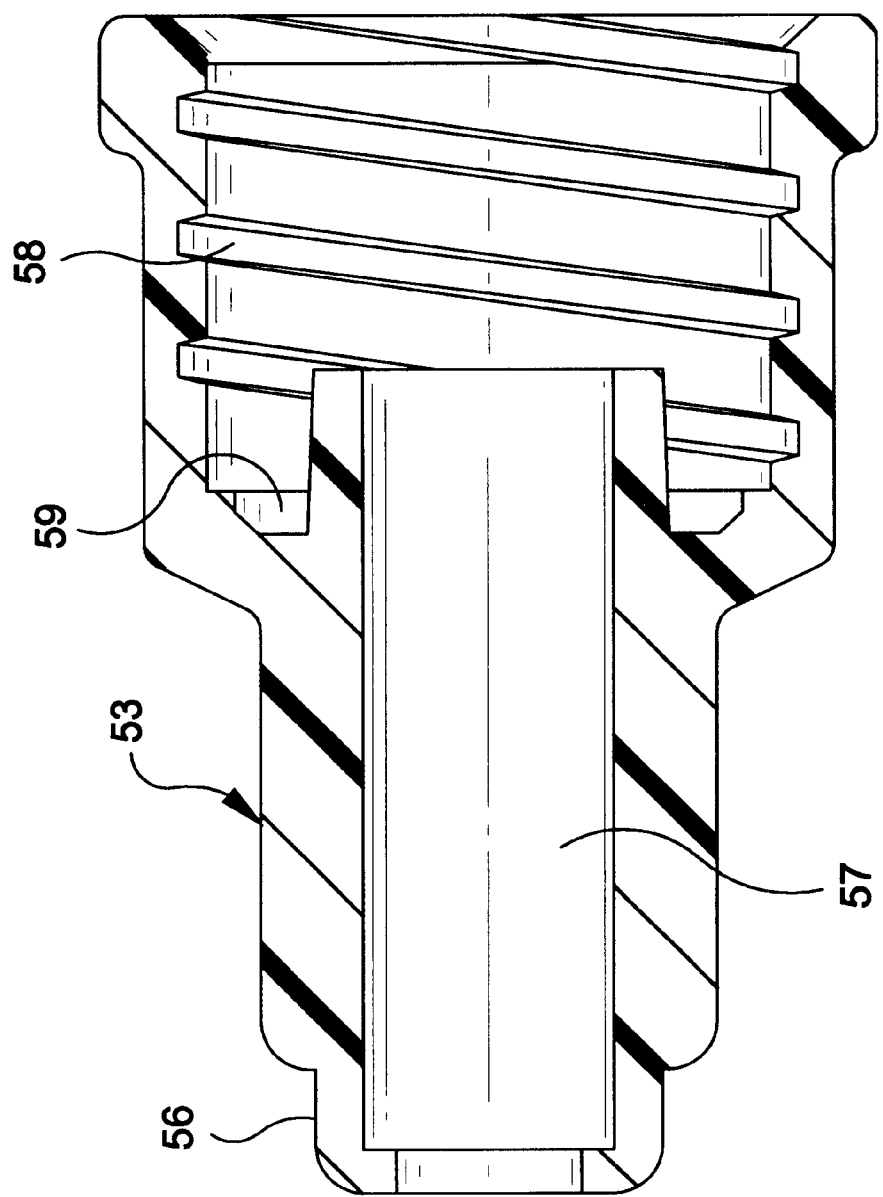
FIG. 5 is an enlarged cross-sectional view of the outer hub of the retracting needle assembly.
Figure 6:
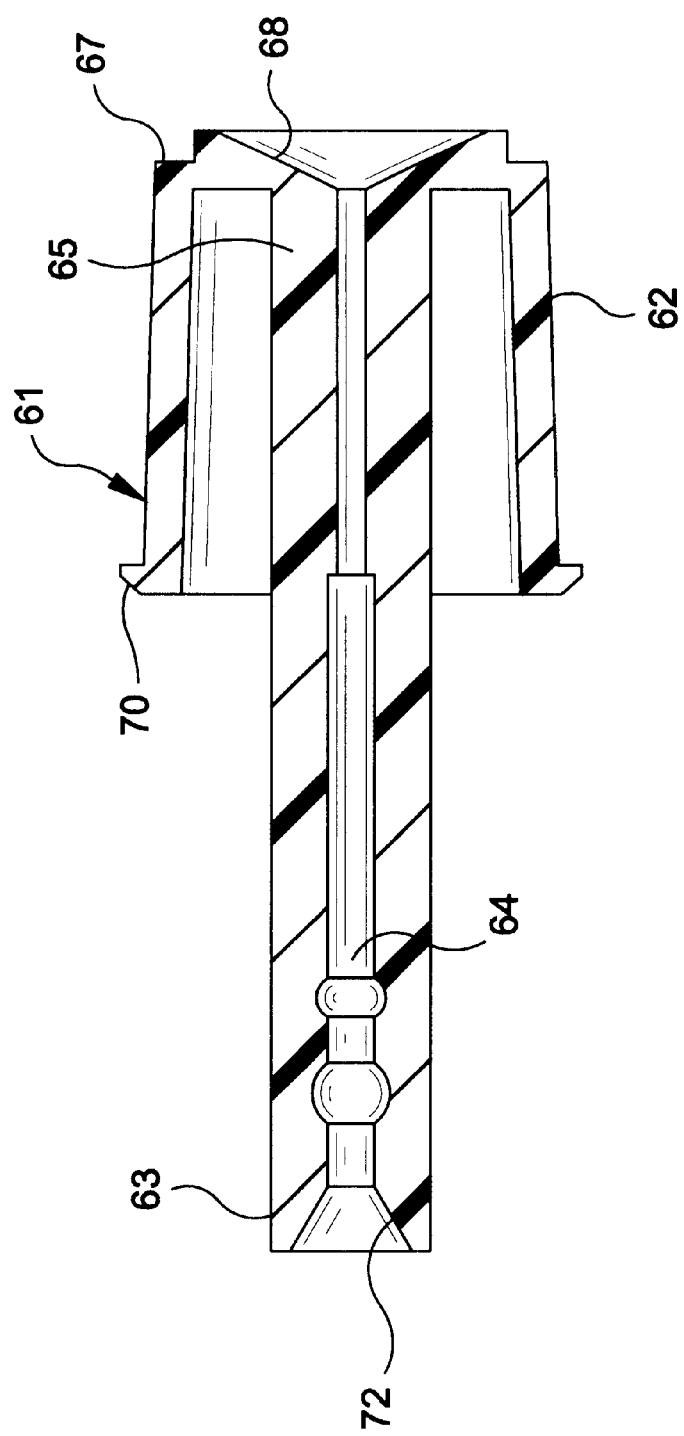
FIG. 6 is an enlarged cross-sectional view of the inner hub of the retracting needle assembly.
Figure 7:
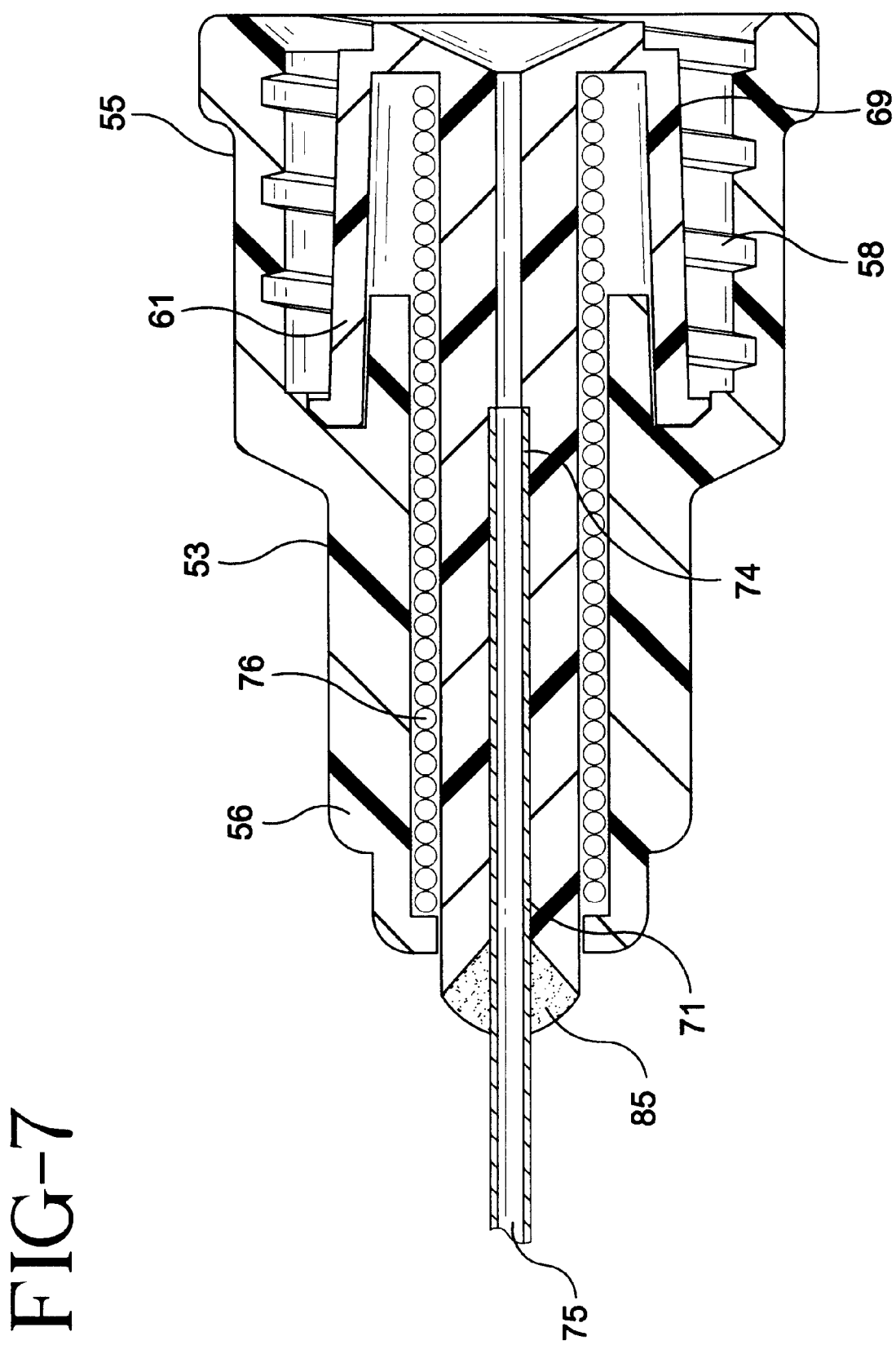
FIG. 7 is an enlarged cross-sectional view of the retracting needle assembly.
Figure 8:
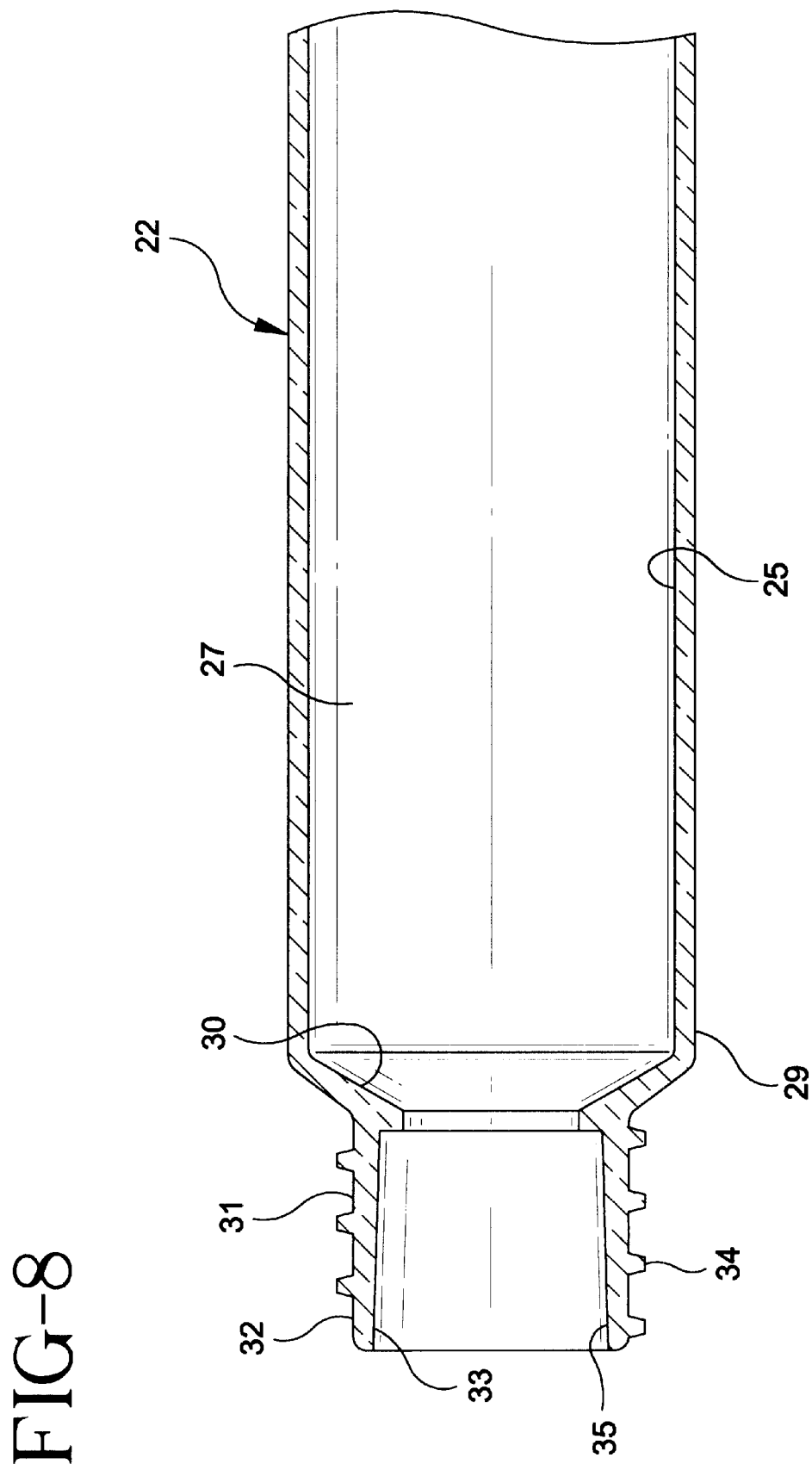
FIG. 8 is an enlarged cross-sectional view of the distal end of the syringe barrel.

While this invention is satisfied by embodiments in many different forms, there are shown in the drawings and will herein be described in detail, preferred embodiments of the invention with the understanding that the present disclosure is to be considered exemplary of the principles of the invention and not intended to limit the scope of the invention to the embodiments illustrated. The scope of the invention will be measured by the appended claims and their equivalents.

Referring to FIGS. 1–11, an operable retracting needle syringe 20 includes a retracting needle assembly 21, a syringe barrel 22 and a plunger 23. The barrel includes an inside surface 25 defining a chamber 27, an open proximal end 28 and an open distal end 29 including a cylindrical collar 31 having an outside surface 32 and an inside surface 33.

The plunger is slidably positioned in fluid-tight engagement with the inside surface of the barrel. The plunger includes a proximal portion 37 having a distal end 38 with an elongated cavity 39 therein. A release element 43 having a sharp distal edge 44 is positioned at distal end 38 of the proximal portion of plunger 23. A hollow distal portion 46 of plunger 23 is releasably connected to proximal portion 37 and capable of telescopic motion with respect to the proximal portion. A cover element on the distal portion seals a distal end 47. In this embodiment the cover element is stopper 50. It is preferred that the cover element be made of an elastomeric material selected from the group of thermoplastic elastomers, natural rubber, synthetic rubber and combinations thereof.

Retracting needle assembly 21 includes an outer hub 53 having a proximal end 55, a distal end 56 and a passageway 57 therethrough.

The retracting needle assembly also includes an inner hub 61 having a proximal end 62, a distal end 63 and a conduit therethrough 64. The inner hub includes an inner portion 65 and a dissociable outer portion 67 connected to the inner portion. The dissociable outer portion is connected to outer hub 53. Distal end 63 of the inner hub is smaller than passageway 57 of the outer hub at distal end 56 and is accessible therefrom and preferably projects distally outwardly therefrom.

A needle cannula 71 having a distal end 73, a proximal end 74 and a lumen 75 therethrough. The proximal end of the cannula is connected to distal end 63 of the inner hub so that the lumen is in fluid communication with conduit 64 of the inner hub. The distal end of the cannula preferably includes a sharp or sharpened distal tip.

An energized spring is contained between the outer and inner hubs and this preferred embodiment the energized spring is a compressed coil spring 76. Various spring types and elastomeric materials and the like can be used to provide a biasing force between the inner and outer hubs with the coil spring being merely representative of these many possibilities all of which are within the purview of the present invention. A coil spring is preferred because of its compact size and the ability to easily design the spring to provide the forces necessary for proper operation of the retractable needle assembly.

During assembly the coil spring is placed over the inner portion of the inner hub and then the distal end of the spring is positioned in the outer hub and the inner and outer hubs are moved toward each other to compress the spring and lock together through the action of annular locking projection 70 on the inner hub and annular locking recess 59 in the outer hub. When the inner hub and outer hub are joined, compressing the coil spring, annular locking projection on the inner hub snaps into annular locking recess 59 in the outer hub. The projection and the recess are shaped so that much less force is required to assemble the components than to reverse the process, thus providing for a permanent locked condition wherein the inner hub and the outer hub are inseparable during normal operating conditions. There are numerous ways to connect the inner and outer hub and the snap-fit arrangement taught herein is merely representative of all of these methods which are within the purview of the present invention. In particular, adhesives, separate metal locking clips, ultrasonic welding, crimping, internally molded locking structure and the like can be used to hold the inner hub and the outer hub together. An important advantage of the present invention, as will be explained in more detail hereinafter, is that the inner hub, the outer hub and the spring can be assembled before the needle cannula is added to the retracting needle assembly. A preferred way to connect the needle cannula to the retracting needle assembly is to place the proximal end of the needle cannula into the distal end of conduit 64 of the inner hub. An enlarged or irregular portion 72 at the distal end of conduit 64 provides a space for adhesive 85 to be placed around the outside of the needle cannula after it is positioned in the conduit.

The retracting needle assembly also includes means for connecting the outer hub to the collar of the syringe barrel. In this preferred embodiment, means for connecting includes structure providing for threadable engagement between the collar and the outer hub. In this preferred embodiment the structure for threadable engagement includes at least one thread 58 in passageway 57 of outer hub 53 and at least one thread 34 on outside surface 32 of the cylindrical collar. The ability to provide a needle assembly which is removably connected to the barrel is an important feature of this embodiment of the present invention. This feature allows flexibility to interchange needle assemblies and syringes to obtain an appropriately sized needle and syringe combination for the desired drug type and injection site. In addition, the structure of the preferred embodiment allows the installation and removal of the needle assembly from the barrel using the same motions required for installation and removal of a standard hypodermic needle from a standard hypodermic syringe so that no additional training is required for the health care worker.

Another important feature of the present invention is providing a retracting needle syringe with low dead space. This means that almost all of the medication in the chamber is expelled from the syringe during the injection process. Many prior art retractable and retracting needle syringes have structure protruding into the chamber for holding and/or releasing the retracting or retractable needle. Much of the medication surrounding these structures is lost and will not be delivered because needle retraction will have begun while the medication is still in the barrel. To minimize medication loss in retracting needle syringes having structure protruding into the chamber the user could begin the needle retracting process while the needle is still within the patient. The needle could still come out of the patient while medication is being delivered and there is a potential for injury to the patient if the needle is moved laterally as the result of the force being applied to initiate the needle retraction process.

To optimize the feature of low dead space in the present invention, the preferred embodiment includes a frusto-conically shaped surface 68 at proximal end 62 of the inner hub which is preferably a recess. This surface is adapted to mate a conically-shaped surface 51 on stopper 50. Surface 51 is preferably a projection. As the medication is driven from the chamber through the lumen of the cannula stopper 50 approaches the distal end of the syringe barrel until the frusto-conically shaped surface on the stopper approaches very closely and preferably contacts the frusto-conically shaped surface on the inner hub. The drawings show a slight gap between these two elements for clarity purposes only, and it is preferred that at the completion of the plunger stroke the surfaces are touching. Also, the distal end of the syringe barrel includes a frusto-conically shaped surface 30 which also approaches and preferably touches the stopper when the plunger is in its distal-most position with respect to delivering medication from the chamber.

The structure for threadable engagement between the collar and the outer hub can include a wide variety of thread-like and bayonette-type structures including a thread on the outside surface of the collar and a thread follower projection on the inside surface of the outer hub which will follow the collar thread as the hub is screwed onto the collar. This structure is similar to the well-known locking luer-type needle assembly and syringe combinations wherein the syringe collar has a thread on its inside surface and the needle assembly has two in outwardly directed projections on the base of its hub for allowing the hub follow the threads of the collar as it is screwed onto the luer tip and collar. Also, the inside of the collar can be threaded in the outside of the outer hub can have thread followers.

One of the issues not well addressed by the prior art is leakage. During use, the contents of the syringe are subject to high pressures, both positive and negative, when trying to draw in and deliver medications, especially with viscous medications. To help prevent leakage, preferably without having to use a gasket, the preferred embodiment includes tapered cylindrical surface 69 on inner hub 61 and tapered cylindrical surface 35 on the inside of cylindrical collar 31 of the barrel. When the retracting needle assembly engages the collar of the barrel, the tapered cylindrical surface 35 on the collar engages tapered cylindrical surface 69 on the inner hub to seal the interface between the hub and the collar to prevent leakage during normal use.

The present invention provides a clear departure and improvement over the prior art by offering features such as leakage protection without the use of gaskets, and low dead-space in combination with a removable retracting needle assembly.

Retracting needle assembly 21 preferably, but not necessarily, includes an elongated needle shield 79 having an open proximal end 80, a distal end 81 and a sidewall 82 therebetween defining a recess 83 in the shield. The shield removably engages the outer hub and covers the needle cannula. The shield helps protect the needle cannula from contamination before use. In this embodiment, the shield preferably frictionally engages portions of outer hub 53. However, it is within the purview of the present invention to provide a shield which engages portions of the syringe barrel.

Figure 9:
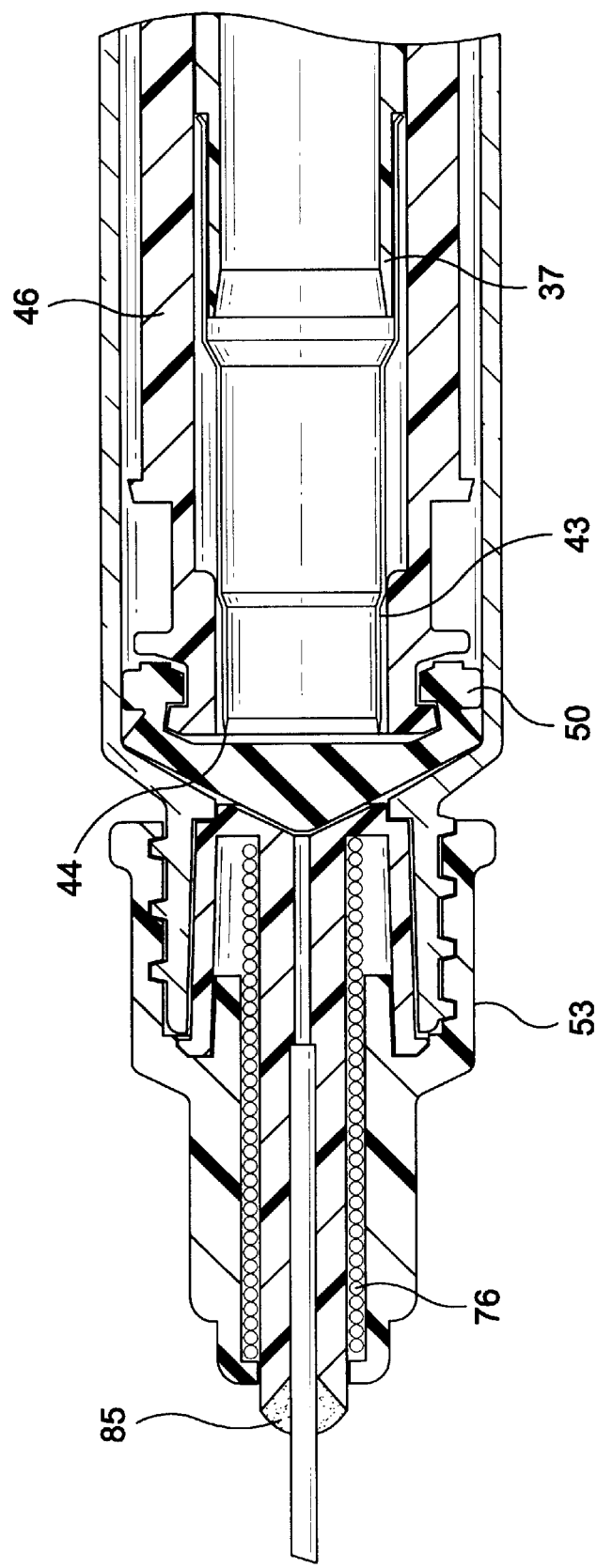
FIG. 9 is a cross-sectional view of the distal end of the syringe and retracting needle assembly of FIG. 1 illustrating the syringe after the liquid contained therein has been delivered.
Figure 10:
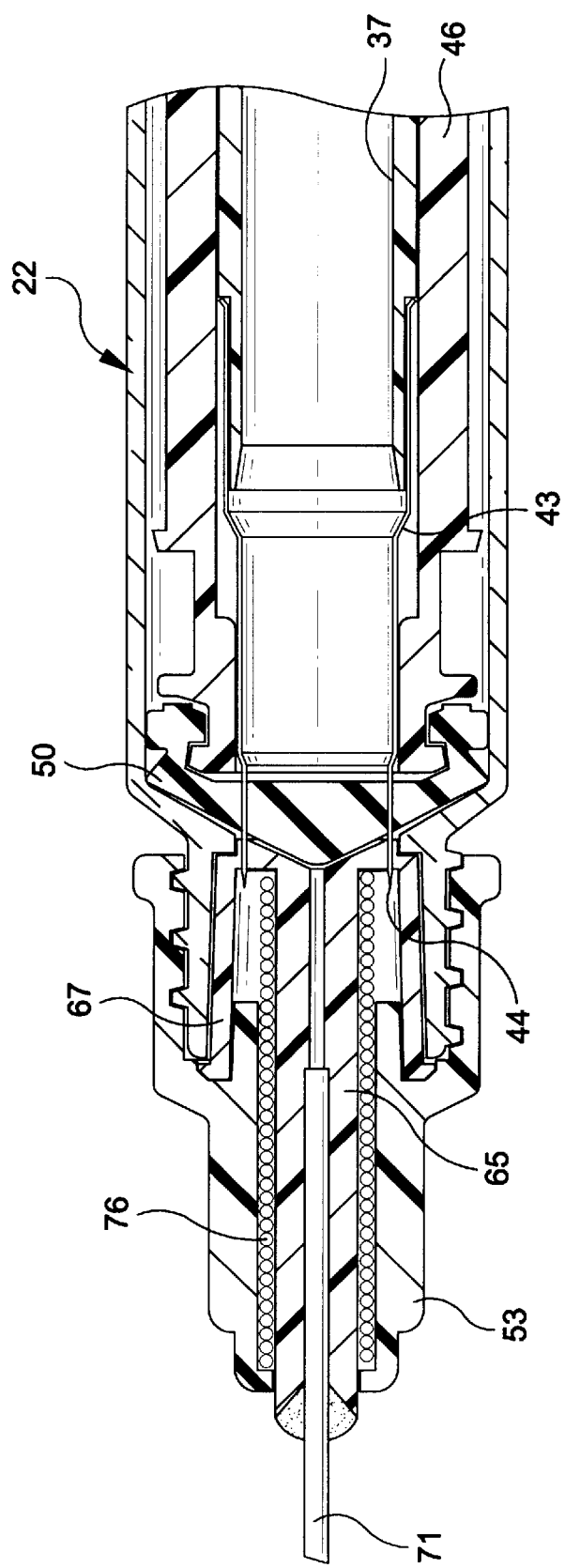
FIG. 10 illustrates the syringe of FIG. 9 when the proximal and distal portions of the plunger rod have separated and release element has cut through the stopper and portions of the inner hub.
Figure 11:
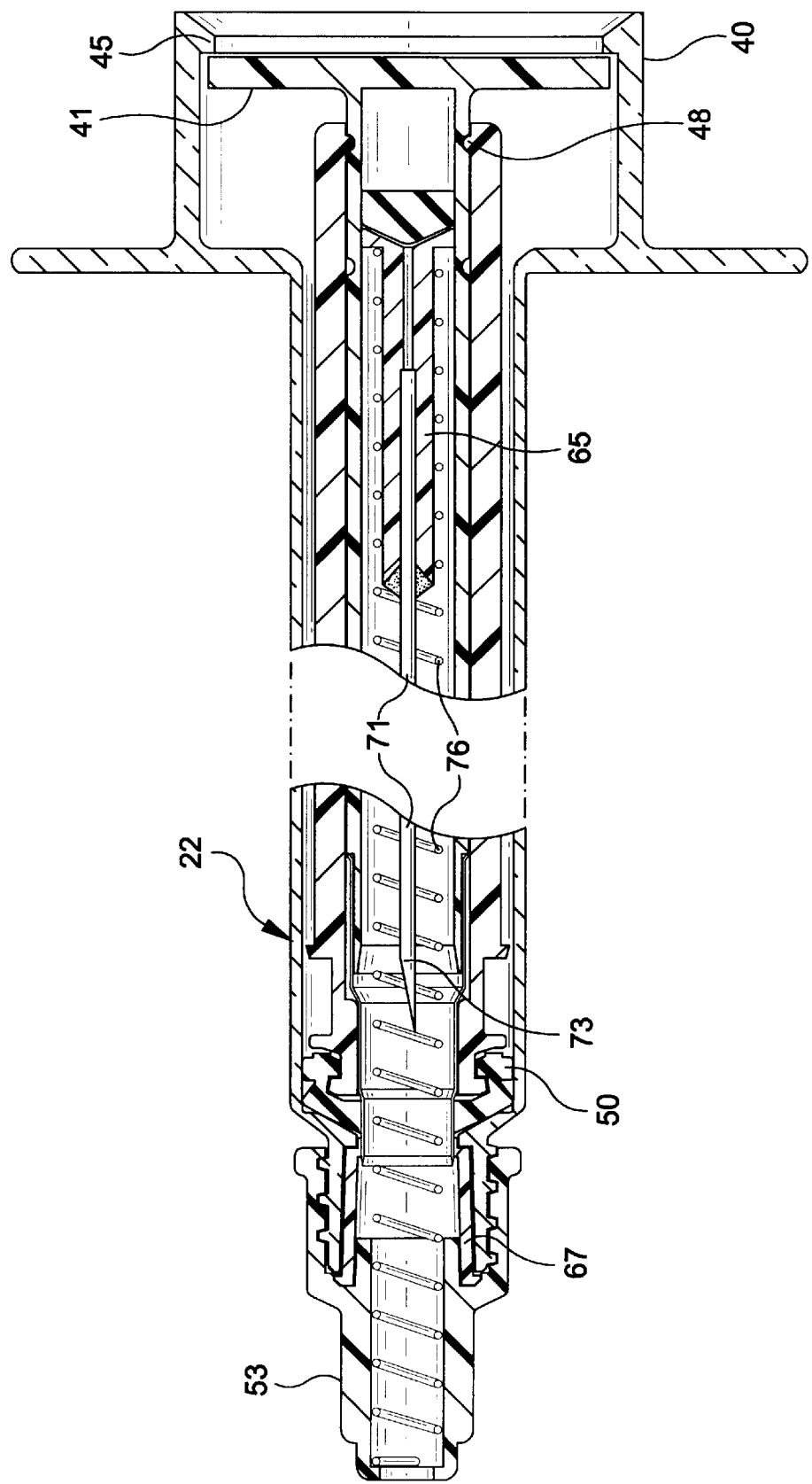
FIG. 11 illustrates the syringe of FIG. 10 when the release element has cut completely through the inner hub and the needle has retracted into the plunger.

In use, the retracting needle assembly of the present invention can be removably connected to syringe barrel 22 containing plunger 23. Needle shield 79 can now be removed from the retracting needle assembly thus exposing the needle cannula for use. The retracting needle syringe can be filled using known methods such as withdrawing injectable liquid from a vial having a pierceable stopper. A syringe may then be used to inject liquid into a patient, an I.V. set, a catheter or other suitable device. After the liquid in the chamber is injected or otherwise delivered, the distal end of the stopper will be contacting the distal end of the barrel chamber as best illustrated in FIG. 9. At this point, the user can apply additional distally directed axial force to the proximal end of the plunger to bottom out the stopper on the distal end of the barrel chamber and to cause the disengagement of the proximal portion 37 of the plunger from distal portion 46 of the plunger. Because the connection between the proximal portion of the plunger and the distal portion of the plunger is broken or overcome, the proximal portion will move distally within the distal portion and along the barrel advancing release element 43 so that its sharp distal end will press on and cut through stopper 50 and through the inner hub between inner portion 65 and dissociable outer portion 67, as best illustrated in FIG. 10. Application of a proximally directed force to the plunger which causes the release element to cut completely through the inner hub, will allow the spring to propel the inner portion of the inner hub along with the needle cannula into the elongated cavity of the plunger as best illustrated in FIG. 11. The used needle cannula is now safely contained within the syringe assembly and ready for safe disposal.

Another feature of the syringe barrel and plunger of the present invention is proximally facing circular wall 40 on the proximal end of the barrel which is slightly larger than flange 41 on the proximal end of the plunger so that when the plunger reaches its furthest distal position with respect to the barrel, the flange 41 is within the circular wall 40 thus preventing the user from attempting to pull the plunger in a proximal direction in an attempt to re-expose the needle. A mechanical interference such as an overlap or snap fit structure can also be provided to further hold the flange inside the circular wall. In this preferred embodiment, inwardly directed ledge 45 is provided to hold the plunger in the barrel after the needle cannula has been retracted. Also, a second groove 48 on the plunger rod can be used to help hold the plunger in the barrel after needle retraction. This second groove is preferably used if an inwardly directed ledge or other structure is not used on circular wall 40. When using second annular groove 48, annular projection 49 on the plunger will engage groove 48 after needle retraction. This engagement will hold the proximal portion of the plunger to the distal portion of the plunger, wherein the distal portion of the plunger will be held in the barrel by the friction of the stopper.

In this preferred embodiment the releasable connection between proximal portion 37 of the plunger and distal portion 46 of the plunger which allows the telescopic relative motion between the two plunger portions is provided by a snap-fit arrangement between the proximal portion of the plunger and the distal portion of the plunger. In particular, an annular projection 49 on the inside of the proximal end of the distal portion 46 of the plunger engages an annular groove 42 on the proximal end of proximal portion 37 of the plunger. When sufficient axial force is applied, annular projection 49 disengages from annular groove 42 allowing the distal end of the release element to cut through the stopper and the inner hub between the dissociable outer portion and the inner portion. There are numerous structures and materials and elements which can provide for a releasable connection between the proximal and distal portions of the plunger with the structure taught hereinabove being merely representative of the many possibilities all of which are within the purview of the present invention. In particular, any combination of projections and/or recesses and/or discontinuities on the proximal portion and the distal portion can accomplish a similar result. Also, the connection can also be breakable as well as disengageable such as by use of a frangible adhesive between the two elements or molding the elements as an integral structure containing a brittle plastic projection or projections which join the elements and can be broken with a force applied to the plunger. A breakable connection can also be made by connecting the elements with a sheer pin. A sheer pin made be made of plastic with one or more notches or stress risers suitably placed to cause breaking at the desired force levels. A breakable connection may also be accomplished similar to the snap fit arrangement but designing the various projections and recesses to fail upon reaching the desired stress level.

Figure 12:
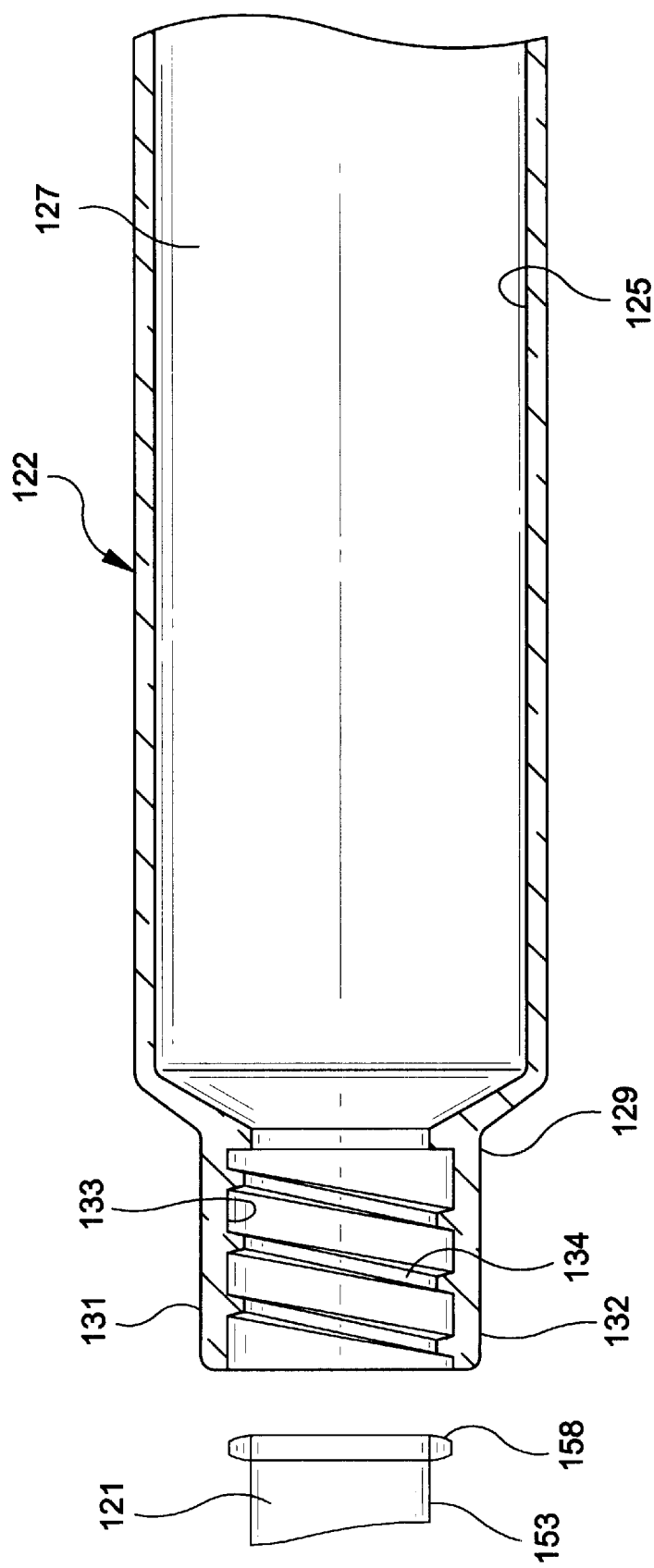
FIG. 12 is an alternative embodiment of the retracting needle assembly and syringe of the present invention.
Figure 13:
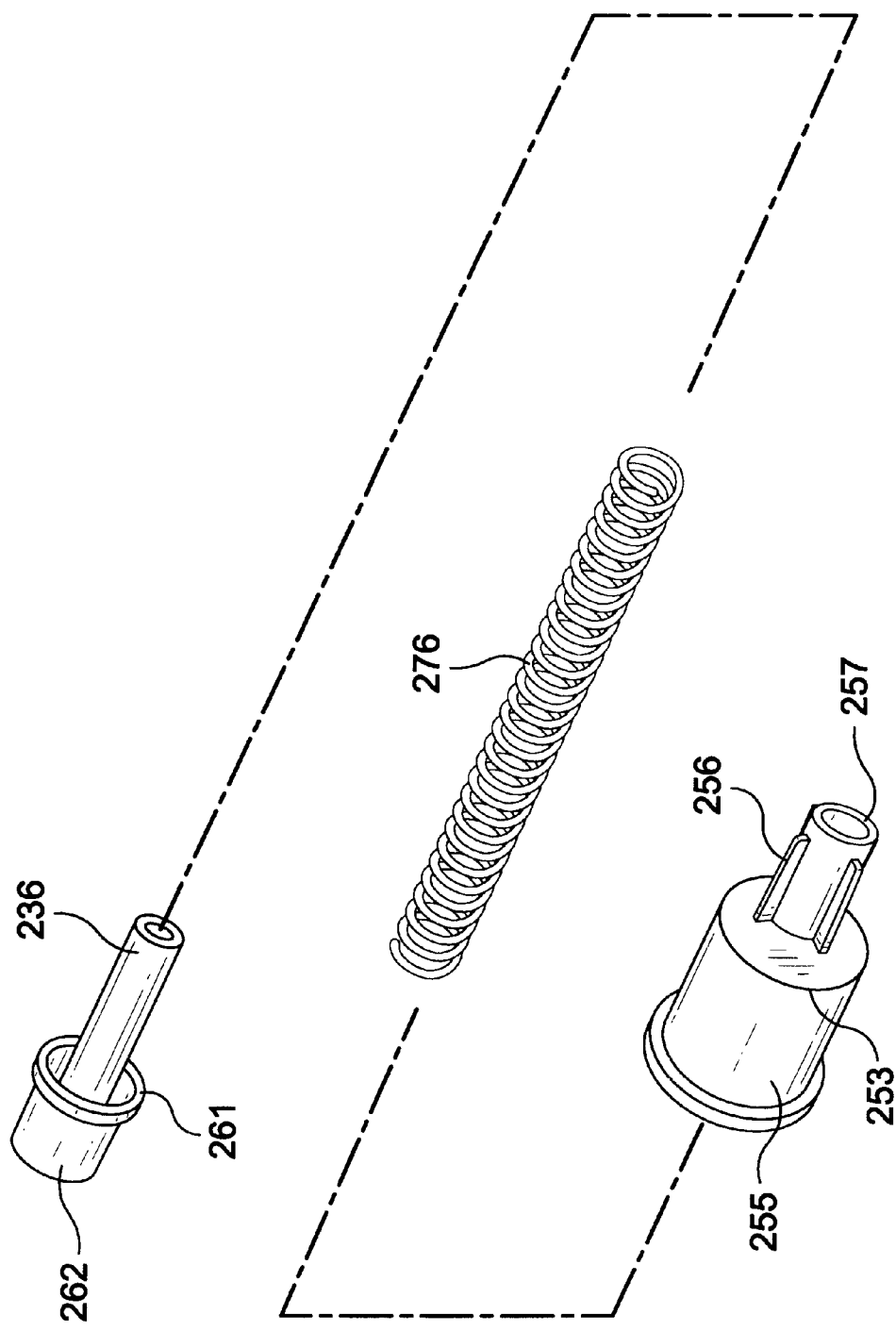
FIGS. 13–17 illustrate a method of making a retracting needle assembly of the present invention.

FIG. 12 illustrates an alternative embodiment of the present invention which functions similarly to the embodiment of FIGS. 1–11 except that means for connecting the outer hub to the collar. In particular, syringe barrel 122 includes an inside surface 125 defining a chamber 127, an open distal end 129, an open proximal end (not shown) and a cylindrical collar 131. The cylindrical collar includes an outside surface 132 and an inside surface 133. The inside surface includes at least one thread 134. A retracting needle assembly 121 includes an outer hub 153 having at least one, and in this preferred embodiment two radially directed outwardly projecting tabs sized and shaped to engage thread 134 so that the retracting needle assembly can be releasably engaged with the syringe barrel through rotational motion of the needle assembly relative to the barrel.

It is also within the purview of the present invention to include means for connecting the outer hub to the collar which is permanent rather than removably engageable. For example, the outer hub can be attached to the collar using adhesive or ultrasonic welding, retaining clips or a one-way snap-fit arrangement that renders the assembly irreversible under normal use. Such structures fall within the purview of the prevent invention.

Referring to FIGS. 13–17, another aspect of the present invention includes a method of making an operable retracting needle assembly. Many prior art retracting needle syringes have a major deficit in that their manufacture requires the needle to be assembled to the needle hub first and then the needle assembly including the needle and the hub is joined with the spring and outer hub or similar structures by placing the spring over the needle and the outer hub over the sharp tip of the needle. This is a difficult task and nearly impossible under high volume manufacturing since the potential for damaging the fragile sharpened distal end of the needle cannula is great. Consequently, these designs may become prohibitively expensive to make under mass production circumstances or yield an unacceptable level of damaged needles which are unsuitable for their purpose or at the very least very painful to the patient. A major improvement provided by the present invention is overcoming the aforementioned shortcomings of prior art retractable needle syringes and w retractable needles. The present invention allows the assembly of the inner and outer hub and the spring before the addition and connection of the sharpened needle cannula. This allows the retracting needle assembly of the present invention to be manufactured in a similar manner to conventional needle assemblies wherein the needle is attached to the finished hub after which there are no further assembly steps but for the application of a needle shield.

Figure 14:
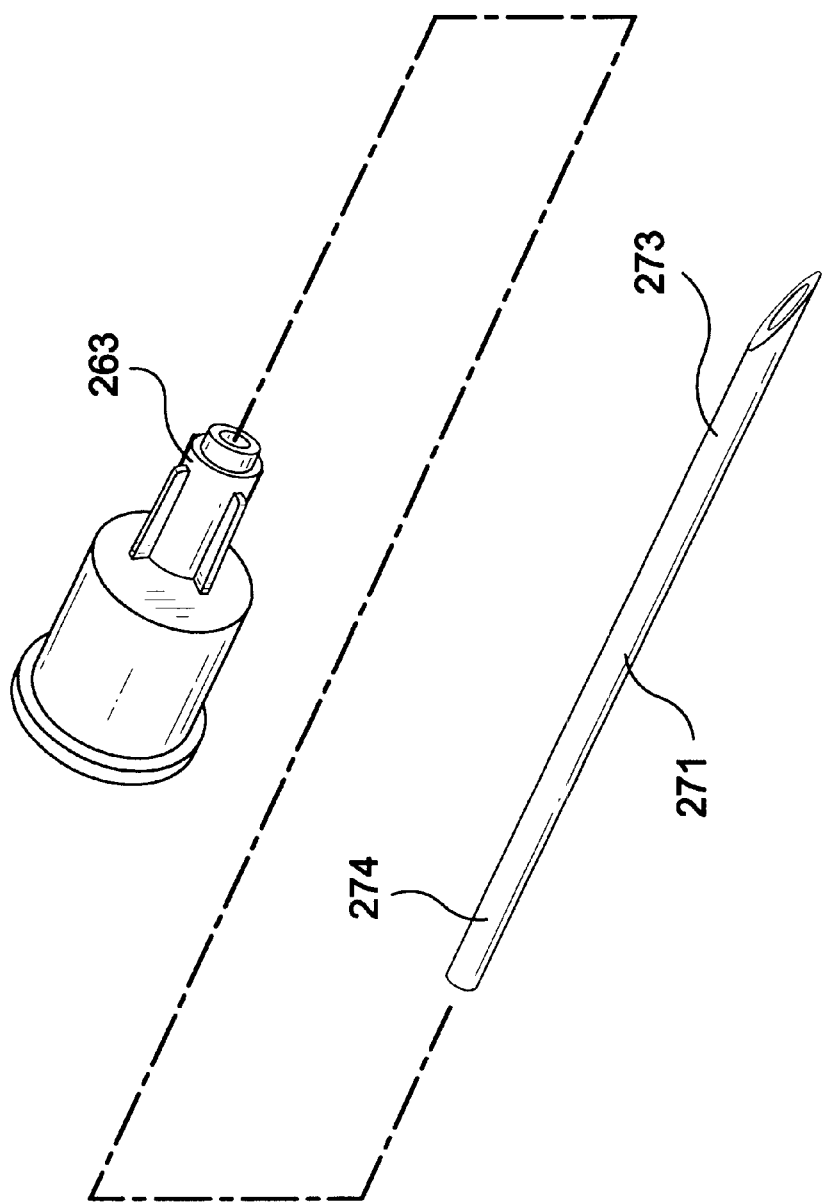
Figure 15:
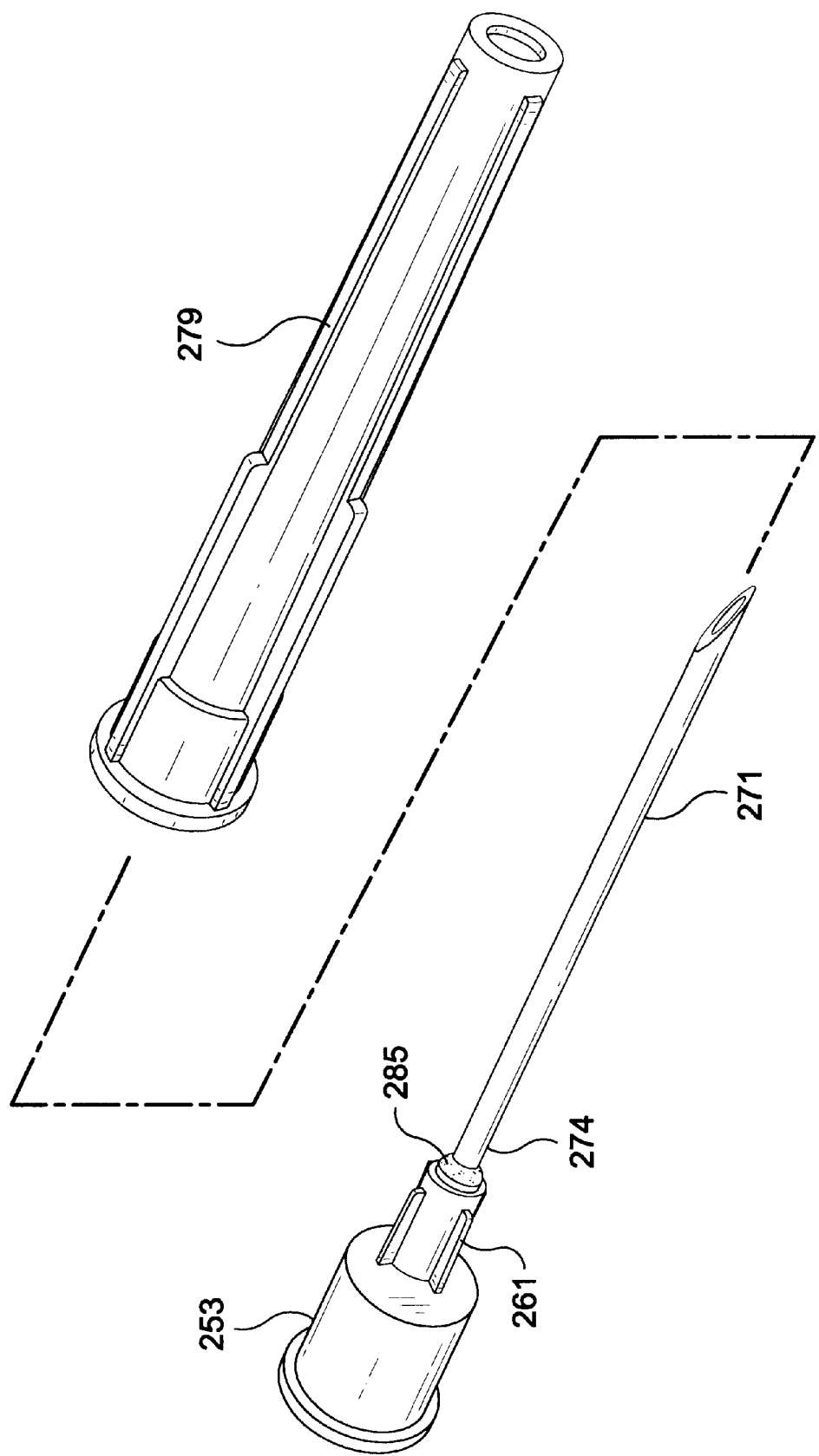
Figure 16:
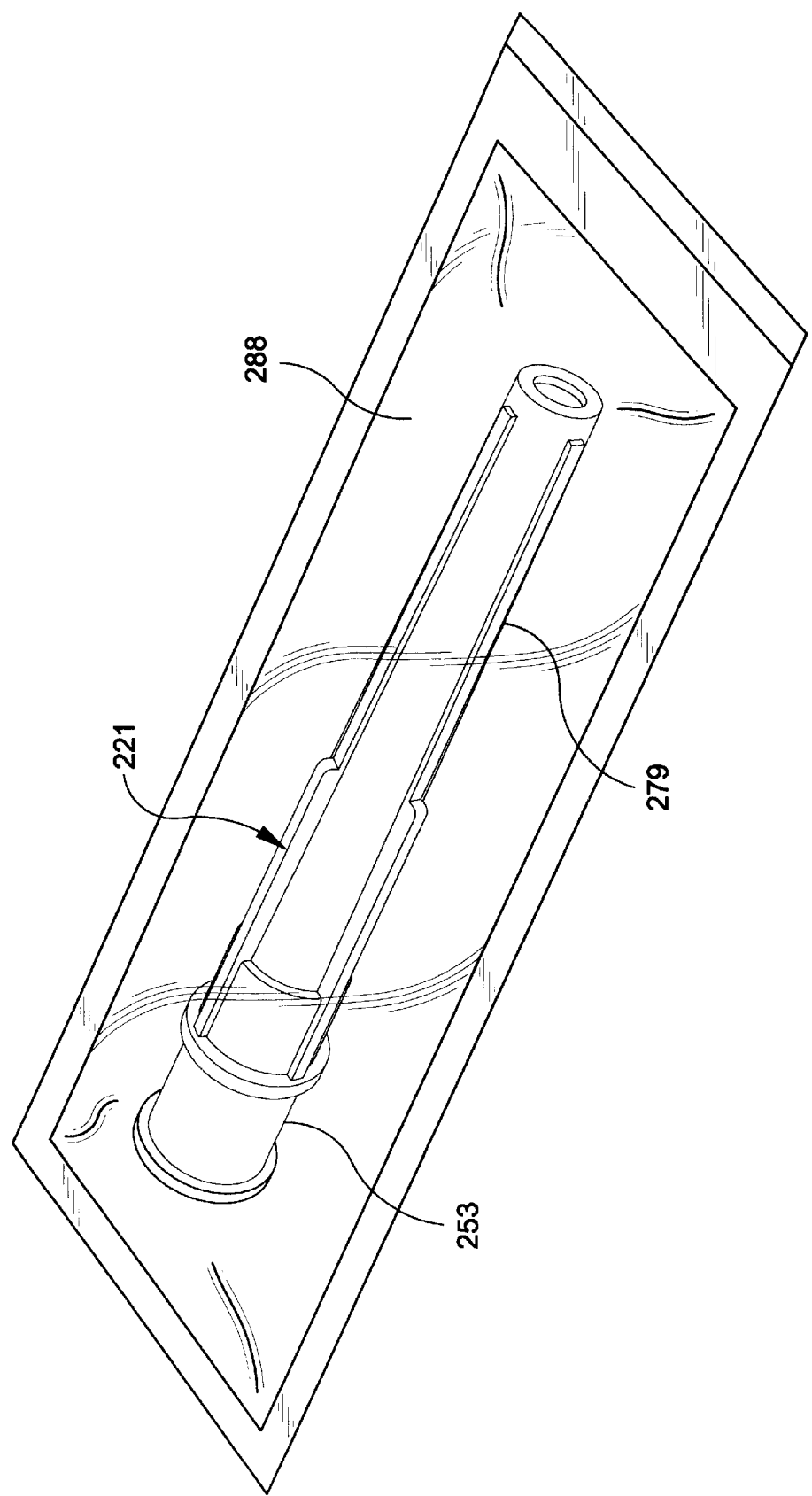
Figure 17:
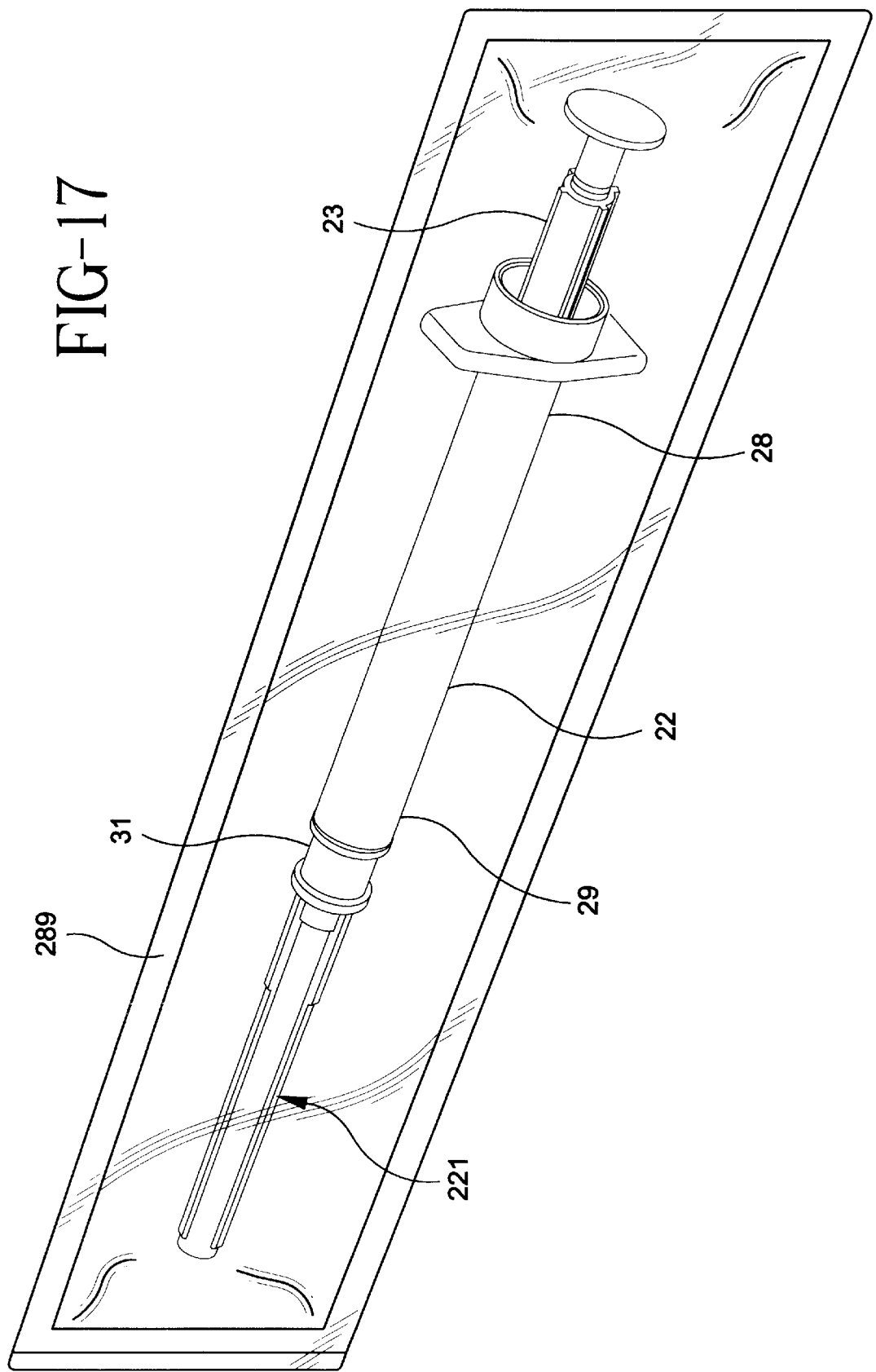

A method of making an operable retracting needle assembly 221 of the present invention comprises the steps of: providing an outer hub 253 having a proximal end 255, a distal end 256 and a passageway 257 therethrough; providing an inner hub 261 having a proximal end 262, a distal end 263 and a conduit therethrough; providing a needle cannula 271 having a distal end 273, a proximal end 274 and a lumen therethrough; providing a coil compression spring 276; assembling the inner hub, the spring and the outer hub so that the spring is compressed and held within the outer hub by the inner hub being connected to the outer hub so that the distal end of the inner hub is accessible from the passageway at the distal end of the outer hub; position proximal end 274 of cannula 271, (as best illustrated in FIG. 14) in the distal end 263 of the conduit in the inner hub; and apply adhesive 285 in the space between the conduit of the inner hub and the needle cannula. A wide variety of adhesives is suitable for attaching a cannula to a hub including epoxy adhesives which may be self-curing or curable with heat, ultraviolet light and the like.

The method of making an operable retracting needle assembly preferably further includes providing an elongated needle shield 279 and removably connecting the needle shield to outer hub 253 so that the distal end of the needle cannula is in the needle shield. At this time, the retracting needle assembly may be sealed in a package 288 which functions as a microbial barrier and sterilized along with the package using a method such as radiation sterilization, autoclaving or the like.

The method of making a retracting needle assembly may also include attaching the needle assembly to a syringe barrel 22 (see FIGS. 1–11) having an inside surface 25 defining a chamber 27, an open proximal end 28 and open distal end 29 including a cylindrical collar 31 so that outer hub 253 engages collar 31. The method may further include providing a plunger 23 either before or after the retracting needle assembly is attached to the syringe barrel. Preferably, this step occurs first before the attachment of the retracting needle assembly. This step includes providing a plunger 23 slidably positioned in fluid-tight engagement with the inside surface of said syringe barrel. At this time, the retracting needle syringe may be sealed in a package 289 which function as a microbial barrier and the package along with the retracting needle syringe is sterilized using a method such as radiation sterilization, autoclaving or the like.

Along with the many structural and functional advantages of the retracting needle assembly and retracting needle syringe of the present invention, the present invention offers a major advantage over the prior art by allowing the needle cannula to be assembled to the retracting needle assembly after the components of the needle assembly have been assembled thereby greatly reducing any potential for damaging the fragile needle tip during the assembly process.

What is claimed is:

1. An operable retracting needle assembly including:
   a syringe barrel having an inside surface defining a chamber, an open proximal end and an open distal end including a cylindrical collar;
   a plunger having a release element with a sharp distal edge;
   an outer hub having a proximal end, a distal end and a passageway therethrough;
   an inner hub having a proximal end, a distal end and a conduit therethrough, said proximal end of said inner hub having an inner portion and a dissociable outer portion connected to said inner portion, said dissociable outer portion connected to said outer hub, said distal end of said inner hub being smaller than said passageway of said outer hub at said distal end of said outer hub and projecting distally outwardly therefrom;
   a needle cannula having a distal end, a proximal end, and a lumen therethrough, said proximal end of said cannula being connected to said distal end of said inner hub so that said lumen is in fluid communication with said conduit;
   an energized spring contained between said outer hub and said inner hub;
   means for connecting said outer hub to the collar of a syringe barrel; and
   wherein distal motion of the plunger in the barrel will cause the sharp distal edge of the release element to cut through the portion of the inner hub which separates the dissociable outer portion from said inner portion, allowing said spring to move said needle cannula in a proximal direction.

2. The assembly of claim 1 further including an elongated needle shield removably engaging said outer hub and covering said needle cannula.

3. The assembly of claim 1 wherein said energized spring is a compressed coil spring.

4. The assembly of claim 1 wherein the cylindrical collar has an outside surface and an inside surface, said outer hub being connected to said collar so that said cannula projects distally outwardly from said syringe barrel.

5. The assembly of claim 4 wherein said means for connecting said outer hub to said collar includes structure for threadable engagement between said collar and said outer hub.

6. The assembly of claim 5 wherein said structure for threadable engagement includes structure on the outside of said collar and in said passageway of said outer hub.

7. The assembly of claim 1 wherein said inner hub includes a frusto-conically-shaped surface adapted to mate with a frusto-conically-shaped surface in said collar for helping to prevent leakage through the interface of said inner hub and said collar.

8. The assembly of claim 1 wherein the plunger is slidably positioned in fluid-tight engagement with the inside surface of the barrel, the plunger including a proximal portion having a distal end with an elongated cavity therein, the release element being positioned at said distal end of said proximal portion, a hollow distal portion releasably connected to said proximal portion and capable of telescopic motion with respect to said proximal portion, a cover element on a distal end of said distal portion sealing said distal end of said distal portion; and wherein distal motion of said plunger with respect to said barrel will cause said proximal portion of said plunger to separate from said distal portion of said plunger allowing said proximal portion to move distally so that said release element contacts and cuts through said cover element and said inner hub disconnecting said dissociable outer portion from said inner portion and allowing said spring to move said needle cannula far enough into said cavity of said proximal portion so that the distal end of the cannula is positioned proximally of the distal end of said outer hub.

9. The assembly of claim 8 wherein said cover element is a stopper having a side portion which contacts said inside surface of said barrel.

10. The assembly of claim 8, wherein said cover element further includes a projection extending outwardly from said cover element, sized and shaped to fit inside a recess in said inner hub.

11. The assembly of claim 8, wherein said stopper is made of an elastomeric material selected from the group of thermoplastic elastomers, natural rubber, synthetic rubber and combinations thereof.

12. An operable retracting needle assembly for use with a syringe barrel having a plunger with a sharp distal edge comprising:

an outer hub having a proximal end, a distal end and a passageway therethrough;

an inner hub having a proximal end, a distal end and a conduit therethrough, said proximal end of said inner hub having an inner portion and a dissociable outer portion connected to said inner portion, said dissociable outer portion connected to said outer hub in said passageway, said distal end of said inner hub being smaller than said passageway of said outer hub at said distal end of said outer hub and projecting distally outwardly therefrom, a frusto-conically shaped surface on said inner hub for sealingly engaging the inside surface of a syringe barrel collar;

a needle cannula having a sharp distal end, a proximal end, and a lumen therethrough, said proximal end of said cannula being connected to said distal end of said inner hub so that said lumen is in fluid communication with said conduit;

a compressed coil spring contained between said outer hub and said inner hub; and means for removably connecting said outer hub to the collar of a syringe barrel.

13. The assembly of claim 12 further including a syringe barrel having an inside surface defining a chamber, an open proximal end and a distal end including a cylindrical collar, said collar having an outside surface with at least one thread thereon and a frusto-conically shaped inside surface, said outer hub being threadably connected to said collar so that said cannula projects distally outwardly from said syringe barrel.

14. The assembly of claim 13 further including a plunger slidably positioned in fluid-tight engagement with said inside surface of said barrel, said plunger including a proximal portion having a distal end with an elongated cavity therein, a release element having a sharp distal edge positioned at said distal end of said proximal portion, an elongated hollow distal portion releasably connected to said proximal portion and capable of telescopic motion with respect to said proximal portion, a cover element on a distal end of said distal portion sealing said distal end of said distal portion; and wherein distal motion of said plunger with respect to said barrel will cause said proximal portion of said plunger rod to break free from said distal portion of said plunger rod allowing said proximal portion to move distally so that said release element contacts and cuts through said cover element and said inner hub disconnecting said dissociable outer portion with said inner portion and allowing said spring to expand and move said needle cannula far enough into said cavity of said proximal portion so that the distal end of the cannula is positioned proximally of the distal end of said outer hub.

15. The needle assembly of claim 12 further including a needle shield.

16. An operable retracting needle assembly including:

a syringe barrel having a distal end and defining a chamber;

a plunger having a sharp distal edge, the plunger being slidably mounted within the chamber;

wherein the plunger defines a cavity;

an outer hub attached to the distal end of the syringe barrel and including a passageway through the outer hub;

an inner hub including an inner portion and a dissociable outer portion connected thereto;

wherein the outer portion of the inner hub is attached to the outer hub;

wherein a conduit is defined through the inner hub;

a needle cannula having a lumen passing therethrough, the needle cannula being mounted to the inner hub so that the lumen is in fluid communication with the conduit;

an energized spring operably engaged to the inner hub and the outer hub;

wherein sliding motion of the plunger in the barrel toward the needle cannula will cause the sharp distal edge to sever the inner portion of the inner hub from the outer portion of the inner hub.

17. The retracting needle assembly of claim 16 further comprising a cover element mounted to the plunger about the sharp distal edge.

18. The retracting needle assembly of claim 17 wherein the cover element has a convex frusto-conically-shaped distal end and the inner hub has a concave frusto-conically-shaped proximal surface, and wherein the distal end of the cover element substantially mates with the proximal surface of the inner hub.

19. The retracting needle assembly of claim 16 wherein the plunger is slidably positioned in fluid-tight engagement with an inside surface of the syringe barrel, and a cover element on a distal end of the plunger sealing said distal end from flow of fluid within the chamber; and wherein distal motion of said plunger with respect to the syringe barrel will cause the sharp distal edge contacts and cuts through said cover element and the inner hub, thereby disconnecting the dissociable outer portion from the inner portion and allowing said spring to move the needle cannula into the cavity.

20. The retracting needle assembly of claim 19 further comprising a flange mounted on a proximal end of the plunger which is sized to fit within a circular wall of the syringe barrel when the plunger is moved to a distal position.

21. The assembly of claim 16 further comprising:

a cover element located on a distal end of said distal portion;

said proximal portion defining an elongated cavity therein, said distal portion being hollow and capable of telescopic motion within said proximal portion, wherein said distal motion of said plunger within said barrel causes said proximal portion to separate from said distal portion causing said distal portion to telescopically move within said proximal portion, distally moving said release element to cut through said cover element and said inner hub, disconnecting said dissociable portion from said inner portion allowing said spring to proximally move said needle within said cavity.

22. The assembly of claim 16, wherein said proximal portion is releasably connected to said distal portion via a snap fit.

23. The assembly of claim 22, wherein said distal portion includes an annular projection at its proximal end and said proximal portion defines an annular groove on its proximal end, wherein said proximal portion is releasably connected to said distal portion via said annular projection engaging said annular groove.

24. The assembly of claim 23, wherein application of an axial force to said plunger causes said distal motion of said plunger disengaging said annular projection from said annular groove.

25. The assembly of claim 16 wherein said proximal portion is releasably connected to said distal portion via a frangible adhesive.

* * * * *